(12) United States Patent
Palanker et al.

(10) Patent No.: US 6,730,075 B2
(45) Date of Patent: May 4, 2004

(54) SURGICAL PROBE FOR USE IN LIQUID MEDIA

(75) Inventors: Daniel V. Palanker, Sunnyvale, CA (US); Alexander Vankov, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 25 days.

(21) Appl. No.: 09/976,849

(22) Filed: Oct. 12, 2001

(65) Prior Publication Data

US 2003/0073986 A1 Apr. 17, 2003

(51) Int. Cl.[7] .............................................. A61B 18/20
(52) U.S. Cl. ................. 606/13; 606/4; 606/45
(58) Field of Search .......................... 606/2, 4, 13, 32, 606/33, 41

(56) References Cited

U.S. PATENT DOCUMENTS

| | | | | |
|---|---|---|---|---|
| 4,693,244 A | * | 9/1987 | Daikuzono | 128/303.1 |
| 5,380,318 A | * | 1/1995 | Daikuzono | 606/16 |
| 5,542,945 A | * | 8/1996 | Fritzsch | 606/48 |
| 5,586,991 A | * | 12/1996 | Yoon | 606/185 |
| 5,658,279 A | | 8/1997 | Nardella et al. | 606/45 |
| 5,697,281 A | | 12/1997 | Eggers et al. | 604/114 |
| 5,697,536 A | | 12/1997 | Eggers et al. | 604/114 |
| 5,891,095 A | | 4/1999 | Eggers et al. | 604/114 |
| 6,066,134 A | | 5/2000 | Eggers et al. | 606/18 |
| 6,135,998 A | | 10/2000 | Palanker | 606/39 |
| 6,164,280 A | * | 12/2000 | Everett et al. | 128/898 |
| 6,213,997 B1 | * | 4/2001 | Hood et al. | 606/5 |
| 6,352,535 B1 | * | 3/2002 | Lewis et al. | 606/45 |
| 6,379,349 B1 | * | 4/2002 | Muller et al. | 606/41 |
| 6,450,970 B1 | * | 9/2002 | Mahler et al. | 600/549 |

* cited by examiner

*Primary Examiner*—Lee Cohen
*Assistant Examiner*—Henry M. Johnson, III
(74) *Attorney, Agent, or Firm*—Lumen Intellectual Property Services, Inc.

(57) ABSTRACT

The present invention provides a surgical probe having a tip for use in liquid media, wherein the tip has a concave body portion and a distal portion. The concave body portion of the tip is positioned immediately adjacent the distal portion such that the liquid jet resulting from the collapse of the cavitation bubble can be substantially reduced. Also disclosed is a surgical probe having a tip and an obstacle for use in liquid media, wherein the tip has a body portion and a distal portion. The obstacle is mounted on the outside of the probe such that the liquid jet resulting from the collapse of the cavitation bubble can be substantially reduced. The obstacle can also be a pick positioned on one side of the probe and in front of the probe.

28 Claims, 15 Drawing Sheets

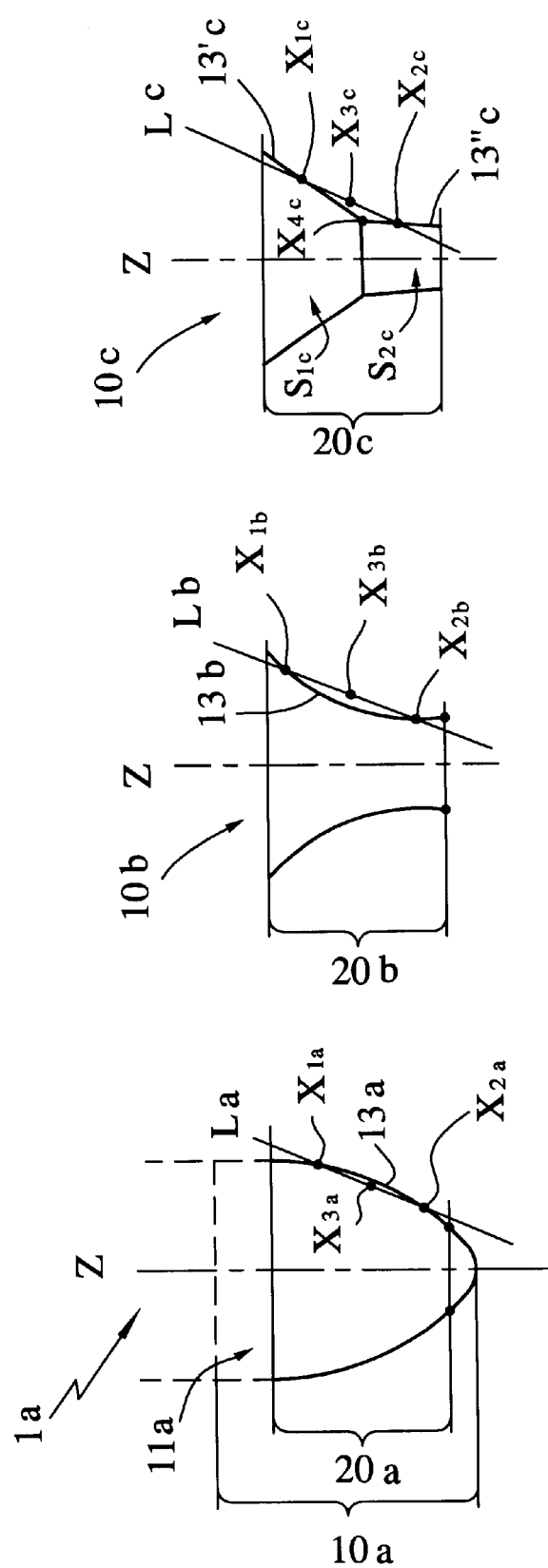

SURGICAL PROBE FOR USE IN LIQUID MEDIA

FIELD OF THE INVENTION

The present invention relates generally to surgical probe for use in liquid media, and in particular to pulsed electrosurgical and laser probe for preventing formation of liquid jet in liquid media.

BACKGROUND OF THE INVENTION

Fiber-delivered laser pulses and pulsed electrical discharges are applied in surgical procedures for precise dissection of soft tissue in liquid media. Energy deposition results from either absorption of the laser radiation in fluid or in tissue, or from localized electric discharge in front of the microelectrode. In liquid media, energy deposition leads to explosive evaporation of fluid and is accompanied by formation of a vapor bubble that can cause substantial collateral damage during its growth and, especially, during the collapse. In fact, collapsing vapor bubbles are the main source of collateral damage in intraocular surgical applications of focused or fiber-delivered pulsed lasers and pulsed electric discharges. When the vapor bubble formed on a tip of an optical fiber probe or on an electric probe collapses, it usually produces a liquid jet in the direction of the probe. This flow of liquid propagates along the axis of the probe and produces tissue damage far beyond the primary energy deposition zone. Repetitive application of laser pulses can also result in formation of a steady flow that pushes soft tissue in front of the probe and interferes with surgery.

"Electrical Alternative to Pulsed fiber delivered Lasers in Microsurgery", Journal of Applied Physics 81(11): 7673–7680 (1997) by Daniel Palanker et al. discloses a method for intracular microsurgery based on cavitation bubble generation by electric discharge. In this approach, the expanding cavitation bubble is used to provide cutting action. A limitation of using the cavitation bubble for cutting is that only very soft tissue (e.g. retinal tissue) can be cut. Relatively hard tissues such as eye lenses, lens capsules (e.g. in a capsulotomy procedure) or irises can not be cut by the method disclosed by Palanker. Yet another disadvantage of the method of Palanker is that cavitation bubbles produce substantial collateral damage to surrounding tissue due to generation of liquid flow during bubble collapse.

U.S. Pat. No. 6,135,998 issued to Daniel Palanker discloses a technique for dissection of tissue by short electric discharge in conducting fluids that create plasma streamers and result in explosive evaporation of water in the vicinity of the probe. Collateral tissue damage in this technique is also associated with collapsing cavitation bubbles.

U.S. Pat. Nos. 6,066,134, 5,891,095, 5,697,536 and 5,697,281 disclose a tip of an electro-surgical probe, wherein the tip has a generally cylindrical body portion, e.g. a portion of a shaft, and a substantially "thin and flat" distal end surface. These prior art references teach that the distal end surface of the tip can be planar, concave, convex, hemispherical, conical and so on in order to facilitate access to certain body structures in electro-surgical procedures. In these prior art references, the body portion of the tip is generally a cylindrical shaft or a blunt shaft (a portion of a convex cone). The geometry of the body portion of the tip (especially the portion just after the distal end surface of the tip) does not play a role in their teachings regarding reducing tissue damage caused by the liquid jet resulting from the collapse of the cavitation bubble.

U.S. Pat. No. 5,658,279 discloses a bipolar electrosurgical tissue penetrating probe having a tip which comprises a conical body portion, or a pyramid body portion, or a blunt body portion, or an annulus body portion. This prior art reference does not discuss situations related to applications of the probe in liquid media. The geometry of the body portion of the tip (especially the portion just after the distal end surface of the tip) also does not play a role in this teaching regarding reducing tissue damage.

In view of the above, it would be an advance in the art to provide a surgical probe for use in liquid media having a novel tip geometry which can substantially reduce or completely eliminate the liquid jet resulting from the collapse of the cavitation bubble so as to substantially lower the tissue damage.

OBJECTS AND ADVANTAGES

In view of the above, it is a primary object of the present invention to provide a surgical probe for use in liquid media having a tip, wherein the tip has a concave body portion and a distal portion, such that the liquid jet resulting from the collapse of the cavitation bubble can be substantially reduced and relevant tissue damage can be substantially lowered or even eliminated.

It is an another object of the present invention to provide a surgical probe having a tip with a concave body portion comprising two or more stages stacked together substantially along the longitudinal direction of the probe.

It is a further object of the present invention to provide a surgical probe for use in liquid media having a tip and an obstacle, wherein the tip has a body portion and a distal portion, such that the liquid jet resulting from the collapse of the cavitation bubble can be substantially reduced or even eliminated and relevant tissue damage can be substantially lowered. The obstacle can be a ring positioned on or after the body portion or a pick positioned on one side of the probe and/or in front of the probe.

These and numerous other objects and advantages of the present invention will become apparent upon reading the detailed description.

SUMMARY

The present invention provides a surgical probe having a tip for use in liquid media, wherein the tip has a concave body portion and a distal portion. The concave body portion of the tip is positioned after the distal portion such that the liquid jet resulting from the collapse of the cavitation bubble can be substantially reduced, or even eliminated.

The present invention also provides a surgical probe having a tip and an obstacle for use in liquid media, wherein the tip has a body portion and a distal portion. The obstacle, e.g. a ring, is positioned on the outside of the probe such that the liquid jet resulting from the collapse of the cavitation bubble can be substantially reduced. The obstacle can also be a pick positioned on one side of the probe and/or in front of the probe.

In accordance with the present invention, by changing the geometrical shape of the tip, the liquid flow caused by collapsing bubbles can be substantially reduced and even inverted. During collapse of the bubble, the liquid flow on the back side of the probe with a convex body portion accelerates more than that on the front since the probe occupies increasingly larger part of the area of the liquid/gas boundary. Thus, such a flow will be decelerated on the outer surface of the concave body portion of the tip of the present invention, where the probe occupies increasingly smaller part of the liquid/gas boundary as the bubble collapses.

The concave body portion of the probe according to the present invention is a portion which has at least a portion of a concave cone with circular generatrix, or at least a portion of a concave cone with elliptic generatrix, or at least a portion of a concave cone portion with parabolic generatrix, or at least a portion of a concave cone with hyperbolic generatrix, or their combinations, or any other regular or irregular concave shapes. The concave body portion can also have two or more stages stacked together substantially along the longitudinal direction of the probe. For example, the concave body portion can have two or more stages (with linear generatrix) selected from the group consisting essentially of cylindrical stage, conical stage and planar stage.

The concave body portion of the tip is generally symmetrical with respect to the longitudinal axis of the probe. However, the concave body portion can also be asymmetrical with respect to the longitudinal axis of the probe.

The dimension of the concave body portion of the tip can be similar to or substantially larger than those of the distal portion of the tip along a longitudinal direction of the tip and the maximal radius of the concave body portion along a horizontal direction of the tip can be similar to or substantially larger than that of the distal portion of the tip.

The distal portion of the tip can be substantially flat, concave, partially concave, convex or partially convex. The distal portion can also have a shape selected from the group consisting essentially of plane, partial-sphere, hemisphere, pyramid, cone and cylinder. Generally, the distal portion of the tip is symmetrical with respect to the longitudinal axis of the probe. However, the distal portion can also be asymmetrical with respect to the longitudinal axis of the probe.

Similar effect of deceleration can be achieved using an obstacle, e.g. a ring, position behind the distal portion of the tip. This ring slows down the flow from the back of the tip thus reducing, eliminating or even inverting the liquid jet in front of the probe.

Formation of the forward-propagating liquid jet can also be prevented by placing an obstacle, e.g. a pick, on one side of and/or in front of the tip. Cavitation bubble is attracted to such an obstacle and collapses on it without forming the forward propagating liquid jet flow.

When working with a probe having an obstacle, the body portion of the tip can have at least a cylindrical portion, or at least a conical portion, or at least a concave portion, or at least a convex portion, or their combinations, or any other regular or irregular body shapes. The body portion of the tip is generally symmetrical with respect to the longitudinal axis of the probe. However, the body portion can also be asymmetrical with respect to longitudinal axis of the probe. The distal portion of the tip can be substantially flat, concave, partially concave, convex or partially convex. The distal portion can have any shape selected from the group consisting essentially of plane, partial-sphere, hemisphere, pyramid, cone and cylinder. Generally, the distal portion of the tip is symmetrical with respect to the longitudinal axis of the probe. However, the distal portion can also be asymmetrical with respect to longitudinal axis of the probe.

In accordance with the present invention, the probe of the present invention can be an electric probe, an optical waveguide probe, any form of their combinations, or any other possible surgical probe for use in liquid media.

The above summary of the present invention is not intended to describe each disclosed embodiment or every implementation of the present invention. The figures and the detailed description more particularly exemplify these embodiments.

BRIEF DESCRIPTION OF THE FIGURES

FIG. 2a is a schematic view illustrating a convex body portion of a tip;

FIG. 2b is a schematic view illustrating a concave body portion of a tip;

FIG. 2c is a schematic view illustrating a concave body portion having two conical stages;

Figure 1C:
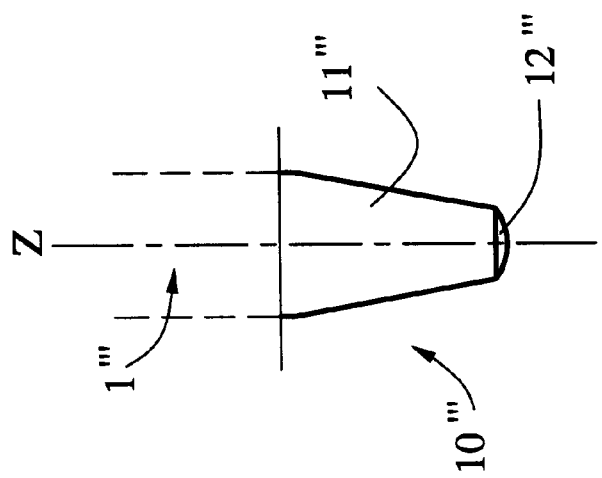
FIG. 1c is a schematic view of a tip of a surgical probe in the prior art with a conical body portion.

While the invention is amendable to various modifications and alternative forms, specifies thereof have been shown by way of examples in the drawings and will be described in detail. It should be understood, however, that the intention is not to limit the present invention to the particular embodiments described. On the contrary, the intention is to cover all modifications, equivalents, and alternatives falling within the spirit and scope of the present invention.

DETAILED DESCRIPTION

The present invention provides a surgical probe for use in liquid media. The geometry of the tip of the surgical probe is novel, e.g. it has a concave body portion, which can substantially reduce or eliminate the liquid jet resulting from the collapse of the cavitation bubble so as to substantially lower the tissue damage.

Figure 1B:
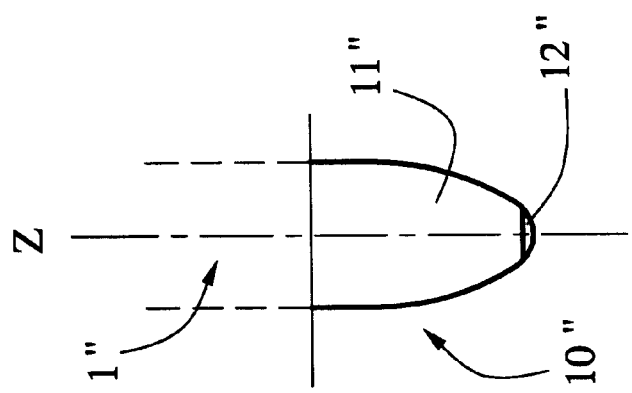
FIG. 1b is a schematic view of a tip of a surgical probe in the prior art with a convex body portion.
Figure 1A:
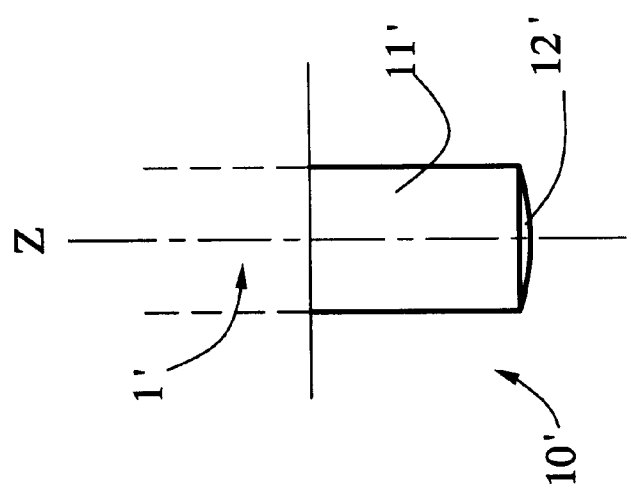
FIG. 1a is a schematic view of a tip of a surgical probe in the prior art with a cylindrical body portion.

FIGS. 1a to 1c illustrate three typical geometrical configurations of a tip of a surgical probe in the prior art. As shown in FIG. 1a, probe 1' has a tip 10' with a cylindrical body portion 11' and a distal portion 12'. In FIG. 1b, the probe 1" has a tip 10" with a convex body portion 11" and a distal portion 12". In FIG. 1c, the probe 1''' has a tip 10''' with a conical body portion 11''' and a distal portion 12'''.

Figure 2F:
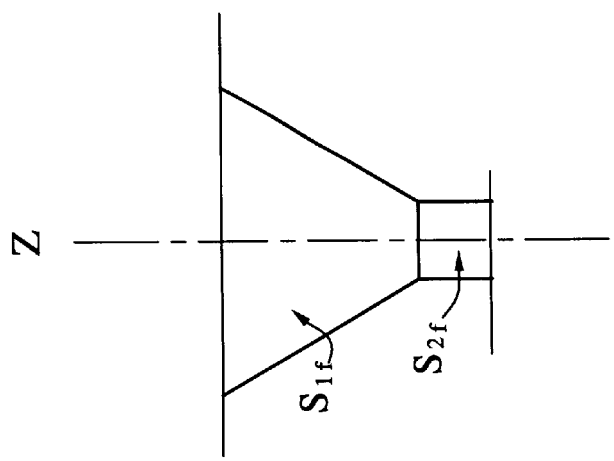
FIG. 2f is a schematic view illustrating a concave body portion having a conical stage and a cylindrical stage.
Figure 2E:
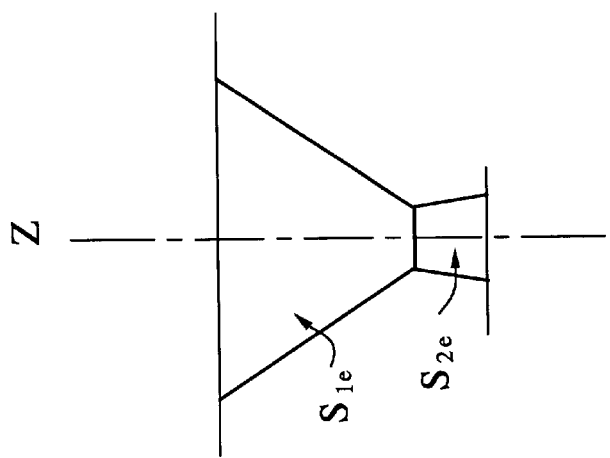
FIG. 2e is a schematic view illustrating a concave body portion having two conical stages.
Figure 2D:
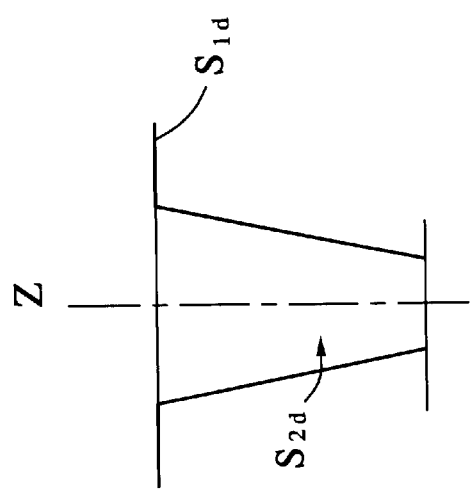
FIG. 2d is a schematic view illustrating a concave body portion having a planar stage and a conical stage.
Figures 3A, 3B, 3C, 3D:
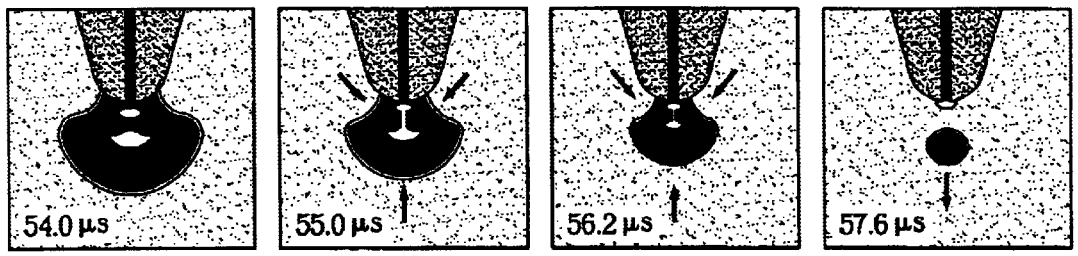
FIGS. 3a–3d are a series of four pictures illustrating the ejection of a collapsing cavitation bubble in forward direction resulting in formation of the axial liquid jet.

The present invention will be best understood by first reviewing the definitions of a concave body portion or a convex body portion of a tip with reference to FIGS. 2a to 2f. FIG. 2a is a sectional view of a portion 20a of the body portion 11a of the tip 10a of a probe 1a. Referring to FIG. 2a, axis Z is the longitudinal axis of the probe 1a and line 13a is a peripheral line or generatrix in the sectional plane containing the axis Z. Point $X_{1a}$ and Point $X_{2a}$ are any two points on line 13a. Line La is a straight line drawn from point $X_{1a}$ to point $X_{2a}$. Point $X_{3a}$ is any point on line La between point $X_{1a}$ and point $X_{2a}$. If point $X_{3a}$ is always inside the surface of the body portion 11a of the tip 10a, this portion 20a of the body portion 11a is a convex body portion. Also, if point $X_{3a}$ in FIG. 2a is always on the surface of the body portion 11a of the tip 10a, this portion 20a of the body portion 11a is a conical body portion, a cylindrical portion or a planar portion.

Referring to FIG. 2b, axis Z is the longitudinal axis of the tip 10b and line 13b is a peripheral line or generatrix in the sectional plane containing the axis Z. Point $X_{1b}$ and Point $X_{2b}$ are any two points on line 13b. Line Lb is a straight line drawn from point $X_{1b}$ to point $X_{2b}$. Point $X_{3b}$ is any point on line Lb between point $X_{1b}$ and point $X_{2b}$. If point $X_{3b}$ is always outside the surface of the tip 10b, this portion 20b of tip 10b is a concave body portion.

According to the present invention, a concave body portion can also be defined by two or more stages stacked together along the longitudinal direction of a probe as shown in FIGS. 2c to 2f. Every stage itself is not necessarily a concave portion. FIG. 2c is a sectional view of a portion 20c of the body portion 11c of the tip 10c, wherein the portion 20c has two stages, $S_{1c}$ and $S_{2c}$. Axis Z is the longitudinal axis of the probe. Line 13c' is a peripheral line or generatrix of stage $S_{1c}$ in the sectional plane containing the axis Z. Line 13c" is a peripheral line or generatrix of stage $S_{2c}$ in the sectional plane containing the axis Z. Point $X_{1c}$ is any point on 13c' (does not include point $X_4$ which is the crossing point of line 13c' and line 13c") and point $X_{2c}$ is any point on line 13c" (does not include point $X_{4c}$). Line Lc is a straight line drawn from point $X_{1c}$ to point $X_{2c}$. Point $X_{3c}$ is any point on line Lc between point $X_{1c}$ and point $X_{2c}$. If point $X_{3c}$ is always outside the surface of the tip 10c, this portion 20c is a concave body portion.

In order to construct a concave body portion, the upper stage can be a conical stage with decreasing diameter towards the distal portion ($S_{1c}$ in FIG. 2c, $S_{1e}$ in FIG. 2e and $S_{1f}$ in FIG. 2f), a planar stage ($S_{1d}$ in FIG. 2d), a concave body portion itself or any other possible regular or irregular shapes. The lower stage can be a conical stage with decreasing diameter towards the distal portion ($S_{2c}$ in FIG. 2c and $S_{2d}$ in FIG. 2d), a conical stage with increasing diameter towards the distal portion ($S_{2e}$ in FIG. 2e), a cylindrical stage ($S_{2f}$ in FIG. 2f), a concave body portion itself or any other possible regular and irregular shape. A concave body portion can be realized by any combination of possible shapes of upper stage and lower stage as long as they fulfill the definition of a concave body portion in accordance with the present invention.

The above definitions of a concave body portion of a tip are only employed to simplify the explanation of the present invention and are not intended to limit the scope of possible shapes of a concave body portion of a tip, but rather to cover all possible, regular or irregular, symmetrical or asymmetrical, bent or straight, shapes of a concave body portion which can fulfill the physical essence of the present invention. The physical essence of the present invention is that a liquid flow resulting from the collapsing of cavitation bubble decelerates on the outer surface of such a concave body portion of a tip so as to substantially reduce the tissue damage.

In a liquid media, energy deposition leads to explosive evaporation of fluid and is accompanied by formation of a vapor bubble that can cause substantial collateral damage during its growth and, especially, during the collapse. In fact, collapsing vapor bubbles are the main source of collateral damage in intraocular surgical applications of focused or fiber-delivered pulsed laser beams and pulsed electric discharges.

Figure 14:
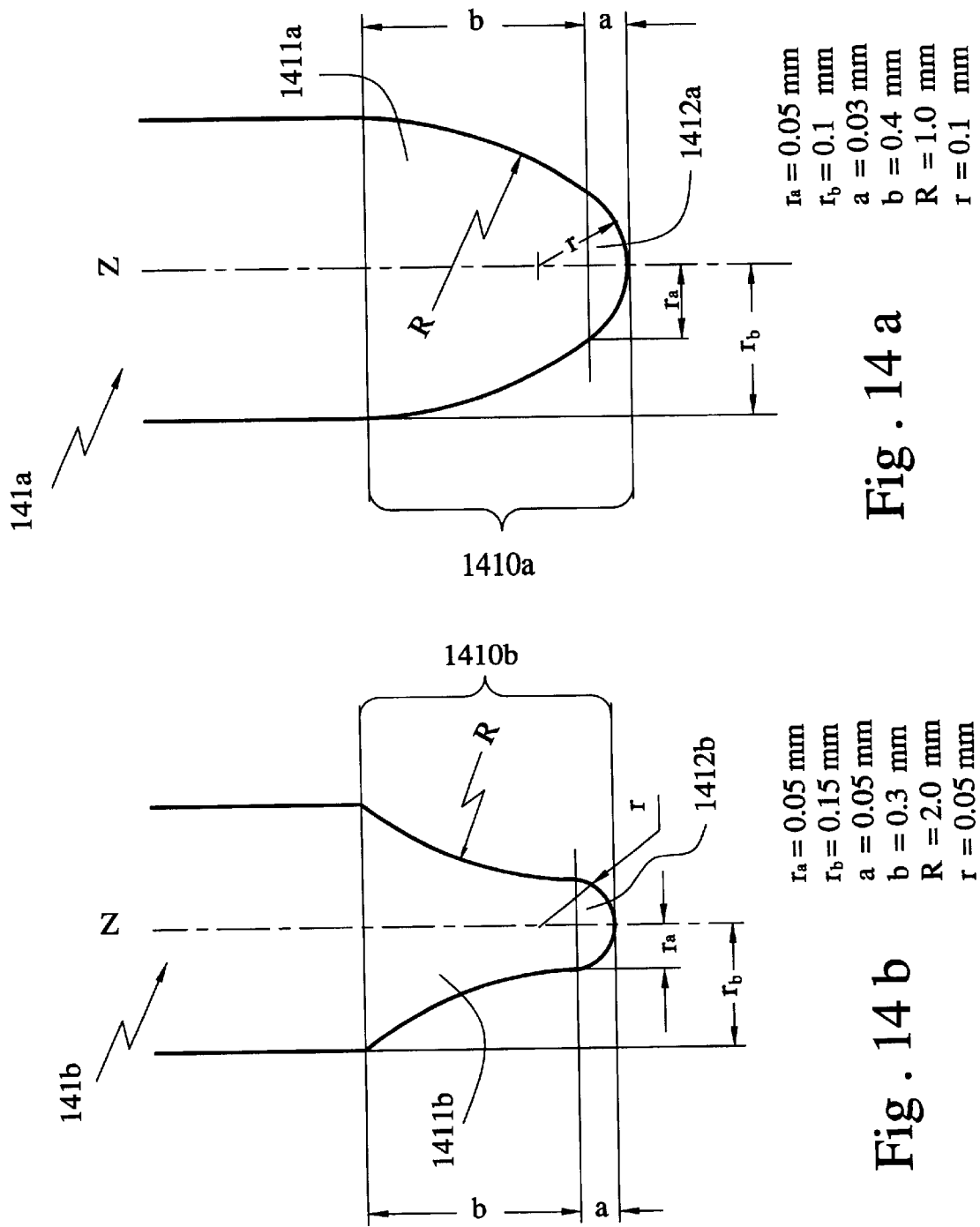
FIG. 14a illustrates the geometrical characteristics of the tip used in the experiment of FIGS. 3a–3d.
FIG. 14b illustrates the geometrical characteristics of the tip used in this experiment of FIG. 5b.

FIGS. 3a–3d are a series of four pictures illustrating the ejection of the collapsing cavitation bubble in forward direction resulting in formation of the axial liquid jet flow within a short period of time as indicated by different moments (µs) under these pictures. As shown in FIGS. 3a–3d, when the vapor bubble formed on a tip of an optical fiber probe or on an electric probe collapses, it often produces a liquid jet in the direction of the probe. This liquid jet flow propagates along the axis of the probe and produces tissue damage far beyond the primary energy deposition zone. Repetitive application of laser pulses can also result in formation of a steady flow that pushes soft tissue in front of the probe and interferes with surgery. FIG. 14a illustrates the geometrical characteristics of the tip used in this experiment, wherein $r_a$=0.05 mm, $r_b$=0.1 mm, a=0.03 mm, b=0.4 mm, R=1.0 mm and r=0.1 mm. In FIG. 14a, the probe 141a has a tip 1410a with a convex body portion 1411a and a distal portion 1412a.

Figure 4:
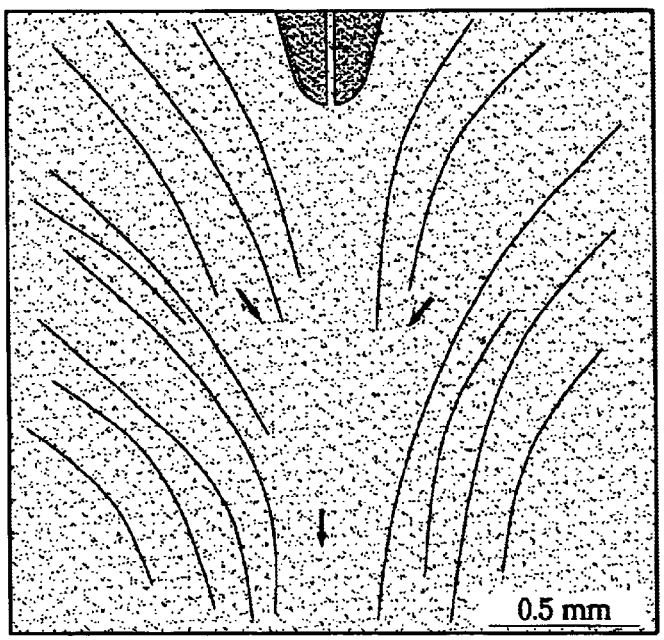
FIG. 4 illustrates the formation of a steady liquid jet flow in saline.
Figure 15:
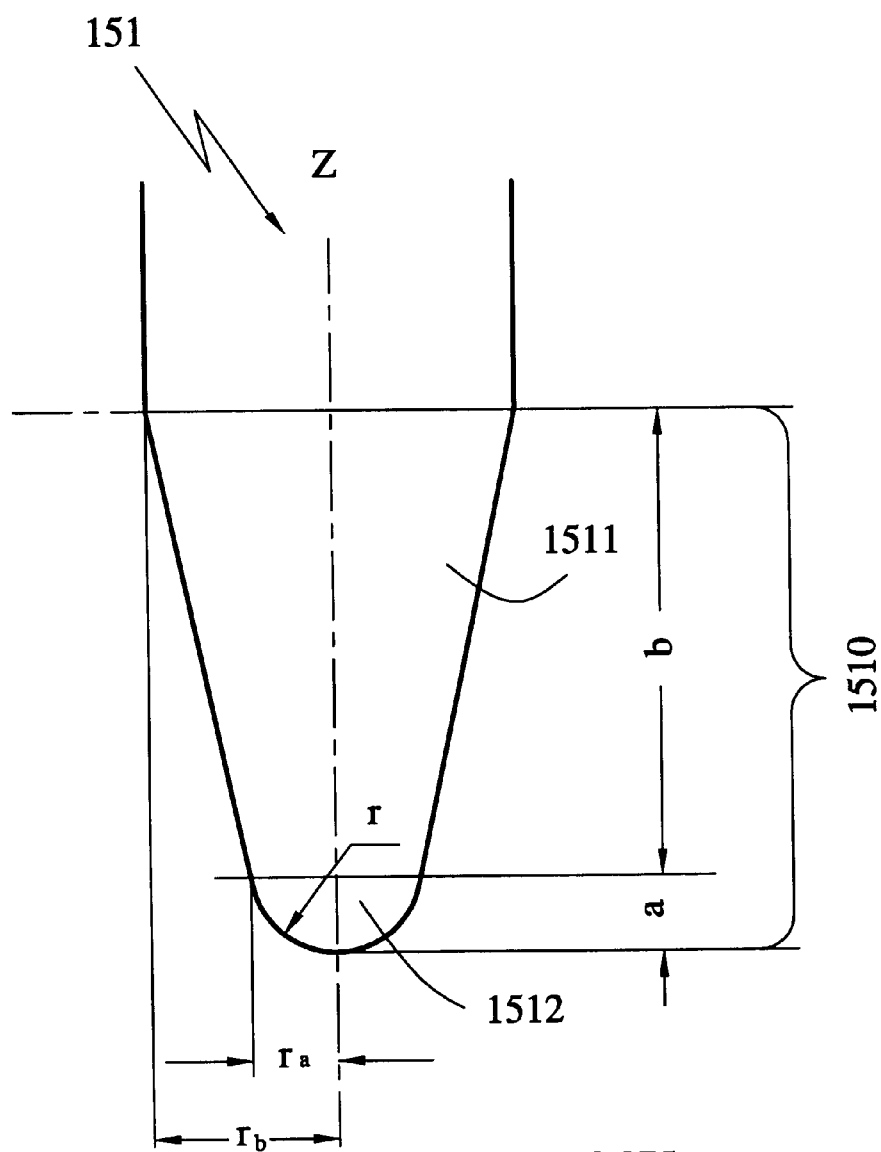
FIG. 15 illustrates the geometrical characteristics of the tip used in the experiment of FIG. 4.

FIG. 4 illustrates the formation of a steady liquid jet flow in saline by application of a train of pulses at energy of 50

μJ/pulse and repetition rate of 20 Hz. The flow is visualized using 6 μm polystyrene beads. FIG. 15 illustrates the geometrical characteristics of the tip used in this experiment, wherein $r_a$=0.075 mm, $r_b$=0.1 mm, a=0.075 mm, b=0.3 mm and r=0.1 mm. In this situation, the maximum radius ($R_{maxbubble}$) of the bubble is about 0.4 mm. In FIG. 15, the probe 151 has a tip 1510 with a conical body portion 1511 and a distal portion 1512.

Figure 5A:
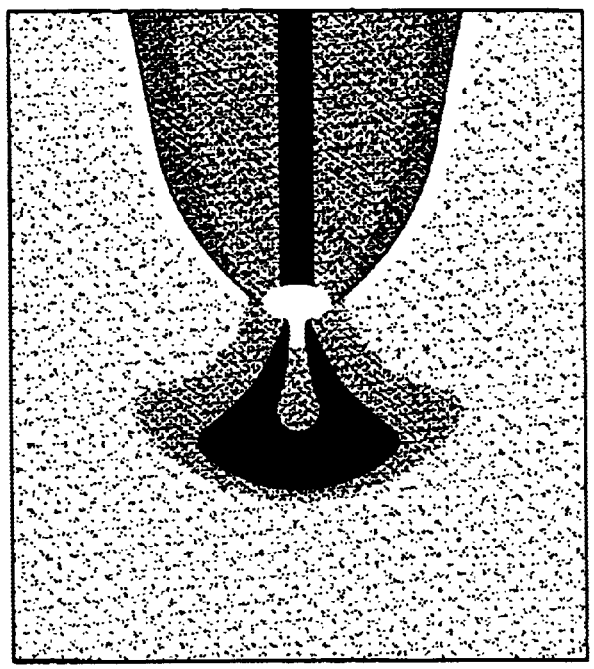
FIG. 5a illustrates the collapsing of a cavitation bubble on a tip with a convex body portion.

FIG. 5a illustrates the collapsing of a cavitation bubble on a tip with a convex body portion. The cavitation bubble in FIG. 5a collapses in a very asymmetric fashion with respect to the horizontal plane, with its back wall moving forward much faster than the front part moves backwards. This effect results in formation of the liquid jet in the forward direction.

Figure 5B:
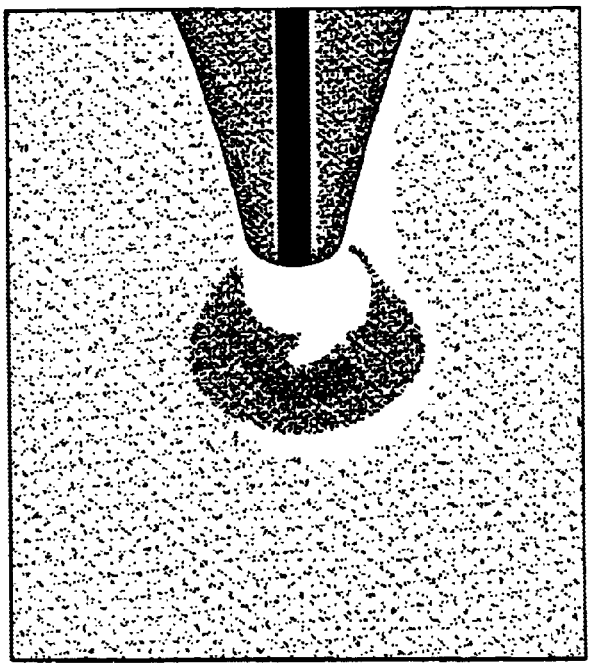
FIG. 5b illustrates the collapsing of a cavitation bubble on a tip with a concave body portion.

FIG. 5b illustrates the collapsing of a cavitation bubble on a tip with a concave body portion. The concave body portion of the tip decelerates the flow from the back part of the tip providing more symmetrical collapsing and thus reducing or preventing the formation of the liquid jet flow. FIG. 14b illustrates the geometrical characteristics of the tip used in this experiment (FIG. 5b), wherein $r_a$=0.05 mm, $r_b$=0.15 mm, a=0.05 mm, b=0.3 mm, R=2.0 mm and r=0.05 mm. In FIG. 14b, the probe 141b has a tip 1410b with a concave body portion 1411b and a distal portion 1412b.

Figure 6A:
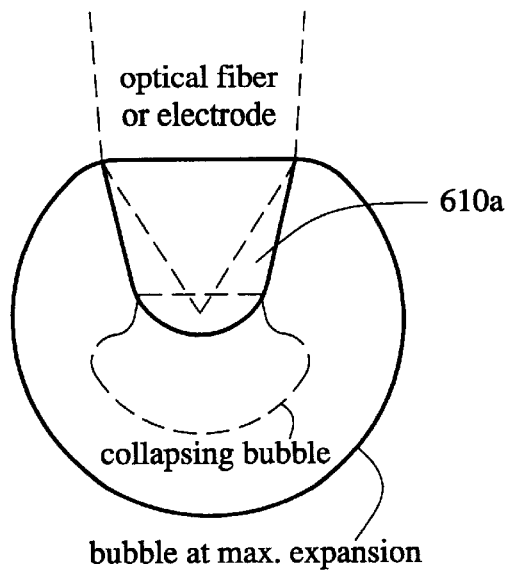
FIG. 6a illustrates the collapsing of a cavitation bubble on a tip with a convex body portion.

FIG. 6a illustrates the collapsing of the cavitation bubble on a tip 610a with a convex body portion. As illustrated, such a tip 610a is wider than a cone with its vortex at the center of the bubble and its base at the line of intersection of the bubble with the tip 610a. With such a tip 610a, the liquid flow from the back is, on average, much faster than that from the front, thus resulting in the formation of a forward-moving liquid jet after the collapse of the bubble.

Figure 6B:
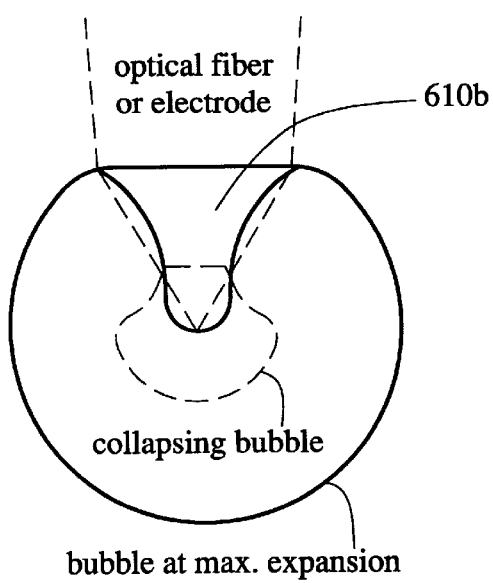
FIG. 6b illustrates the collapsing of a cavitation bubble on a tip with a concave portion.

FIG. 6b illustrates the collapsing of the cavitation bubble on a tip 610b with a concave body portion. The volume inside the bubble of the tip 610b having a concave body portion is substantially the same as or smaller than the cone. The concave body portion slows down the flow from the back as compared with flow from the front, thus substantially reducing or eliminating the liquid jet flow.

Figure 6C:
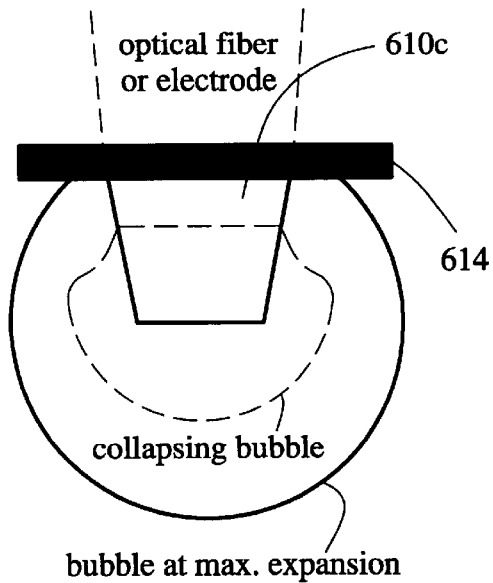
FIG. 6c illustrates the collapsing of a cavitation bubble when using an obstacle.

FIG. 6c illustrates the collapsing of the cavitation bubble on a tip 610c with a body portion and an obstacle 614 positioned on the back part of the body portion. The obstacle 614 in FIG. 6c can be a ring or other shape protruding out of the body portion positioned preferably at a distance close to the radius of the bubble at its maximum expansion phase. The lower surface of the obstacle 614 and the outer surface of the body portion cooperate with each other to create an effect similar to that of a concave body portion (also see FIG. 2d, the lower surface can be recognized as a planar stage $S_{1d}$ in FIG. 2d). This configuration also reduces the velocity of the flow from the back thus reducing or eliminating the liquid jet flow.

Figure 7:
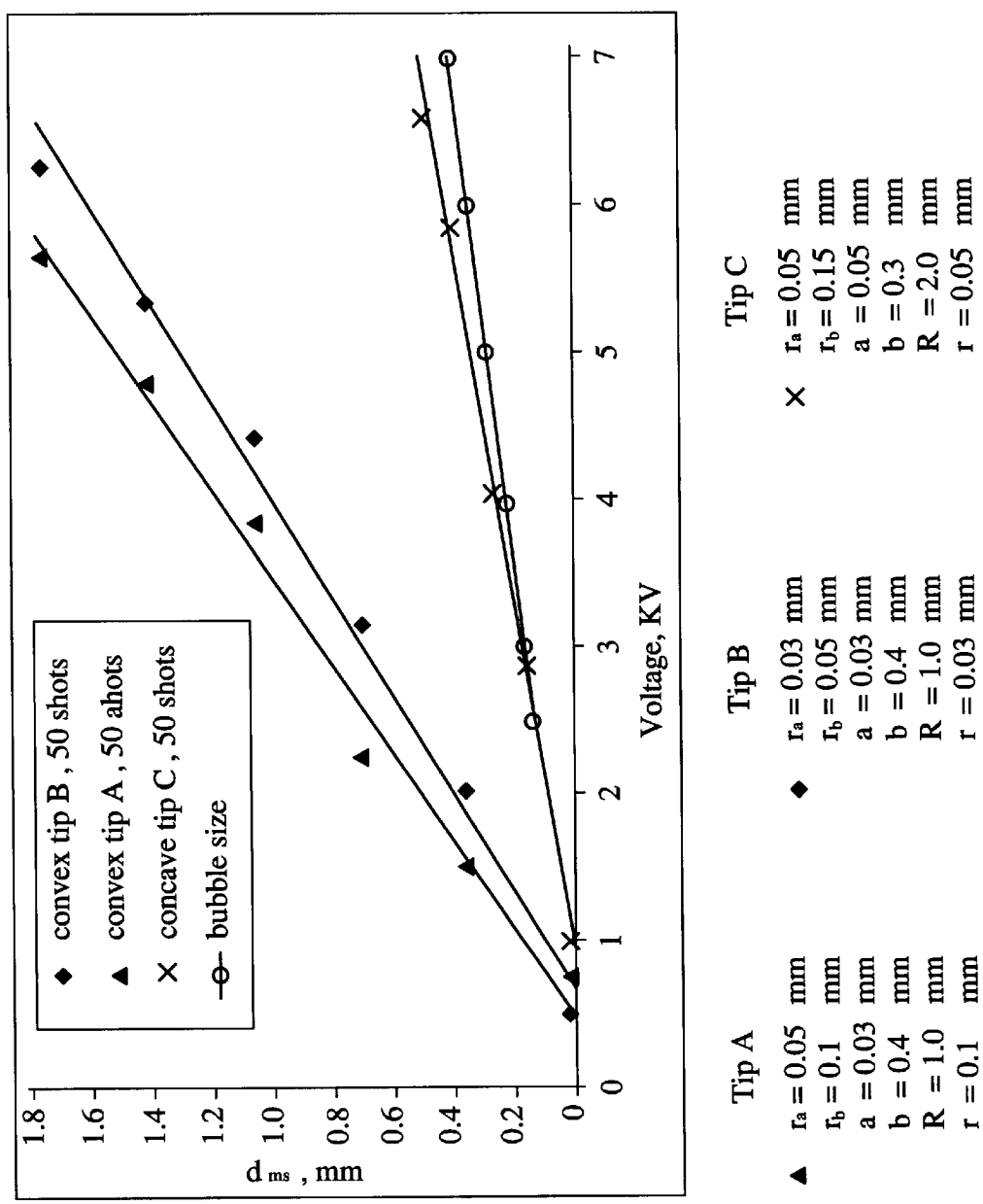
FIG. 7 illustrates minimal safe distance measured on chorioallantoic membrane of chick embryo with various tips in saline using propidium iodide staining.
Figure 8A:
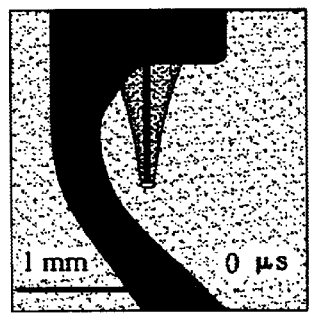
FIGS. 8a–8f are a series of six pictures illustrating the forming and collapsing of a bubble when working with a pick.
Figure 8B:
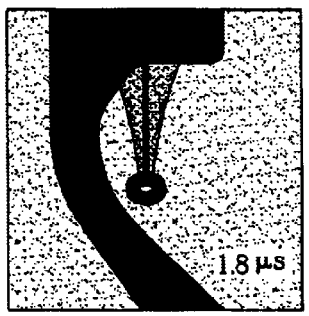
Figure 8C:
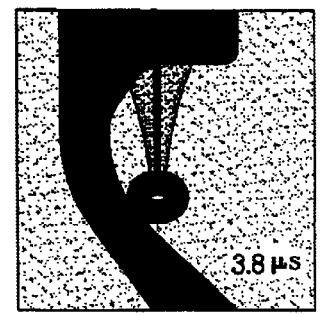
Figure 8D:
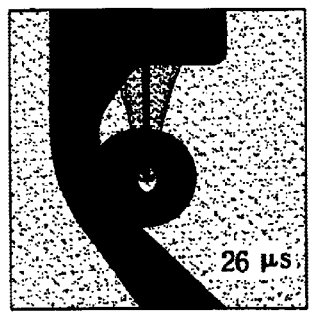
Figure 8E:
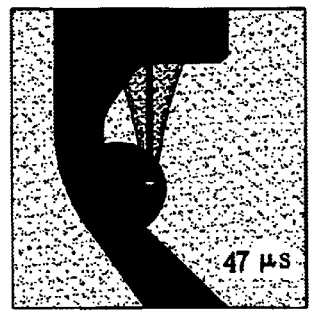
Figure 8F:
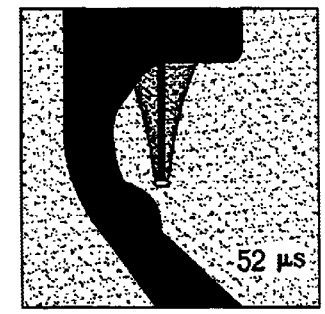

FIG. 7 illustrates minimal safe distance $d_{ms}$ measured on chorioallantoic membrane of chick embryo with three different tips in saline using propidium iodide staining. Fifty pulses are applied at 5 Hz in each position. The minimal safe distance $d_{ms}$ is the maximal distance between the tip and the biological tissue at which the damage is produced by collapsing cavitation bubble. The results in FIG. 7 show that bubble ejection can be completely eliminated using tip (tip C) with a concave body portion and the damage distance can be reduced to the radius of the bubble (indicated as bubble size in FIG. 7). In FIG. 7, the tip A has the same geometrical configuration as the tip in FIG. 14a, wherein $r_a$=0.05 mm, $r_b$=0.1 mm, a=0.03 mm, b=0.4 mm, R=1.0 mm and r=0.1 mm. The tip B also has the same geometrical configuration as the tip in FIG. 14a, wherein $r_a$=0.03 mm, $r_b$=0.05 mm, a=0.03 mm, b=0.4 mm, R=1.0 mm and r=0.03 mm. The tip C has the same geometrical configuration as the tip in FIG. 14b, wherein $r_a$=0.05 mm, $r_b$=0.15 mm, a=0.05 mm, b=0.3 mm, R=2.0 mm and r=0.05 mm.

Figure 16:
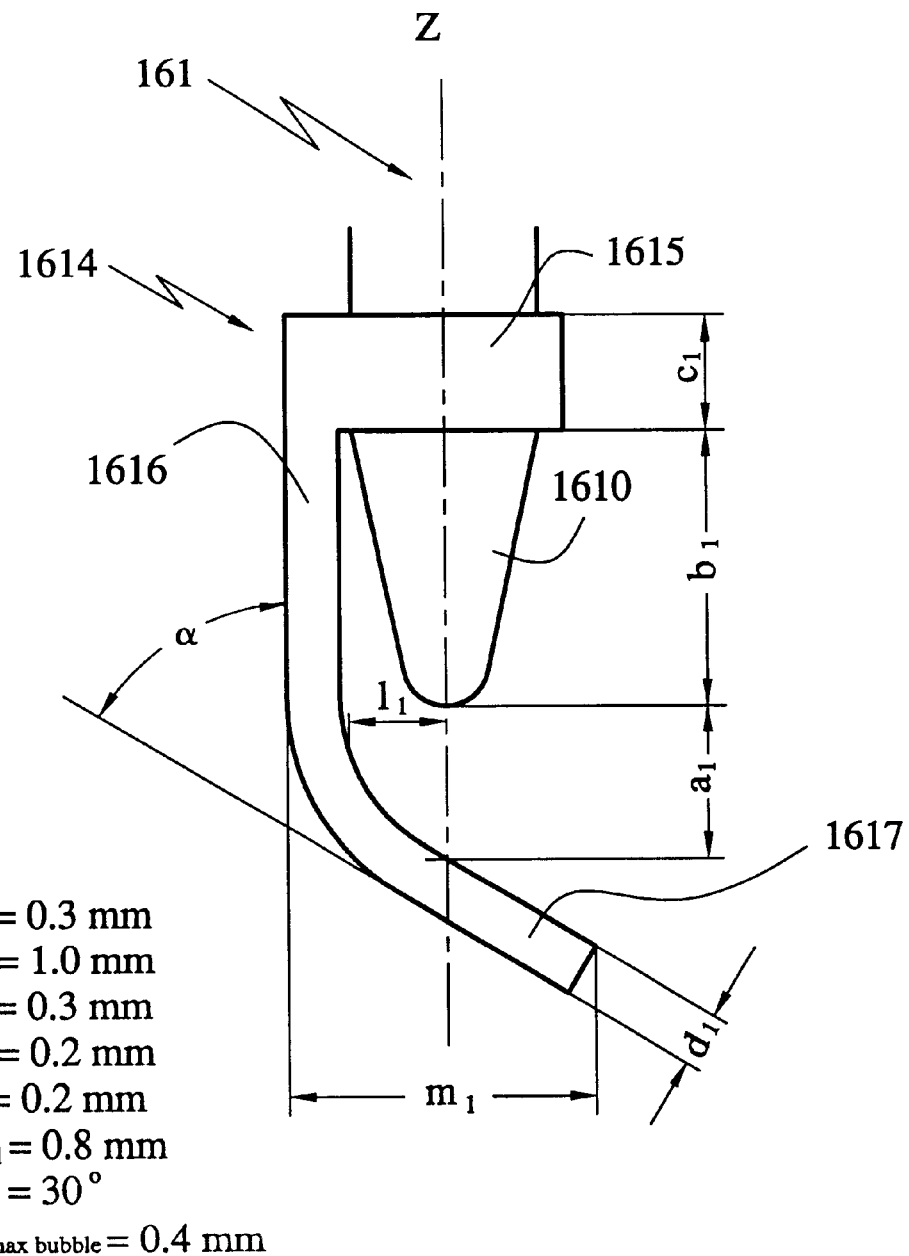
FIG. 16 illustrates a geometrical configuration of a tip having a pick of the present invention.

Formation of the forward-propagating liquid flow can also be prevented by placing an obstacle, e.g. a pick, for the flow on one side of or in front of the tip. FIGS. 8a–8f are a series of six pictures showing the formation and collapse of the cavitation bubble within a short period of time as indicated by different moments (μm) under each of the pictures when using a pick. During collapsing phase, the bubble is attracted to the solid boundary and the forward-propagating flow is not formed. FIG. 16 illustrates a geometrical configuration of a tip with a pick used in the experiment of FIGS. 8a–8f, wherein $a_1$=0.3 mm, $b_1$=1.0 mm, $c_1$=0.3 mm, $d_1$=0.2 mm, $l_i$=0.2 mm, $m_1$=0.8 mm and α=30°. In this situation, the maximum radius ($R_{maxbubble}$) of the bubble is about 0.4 mm. The tip 1610 itself in FIG. 16 has the same geometrical configuration as the tip 1510 in FIG. 15.

Figure 9:
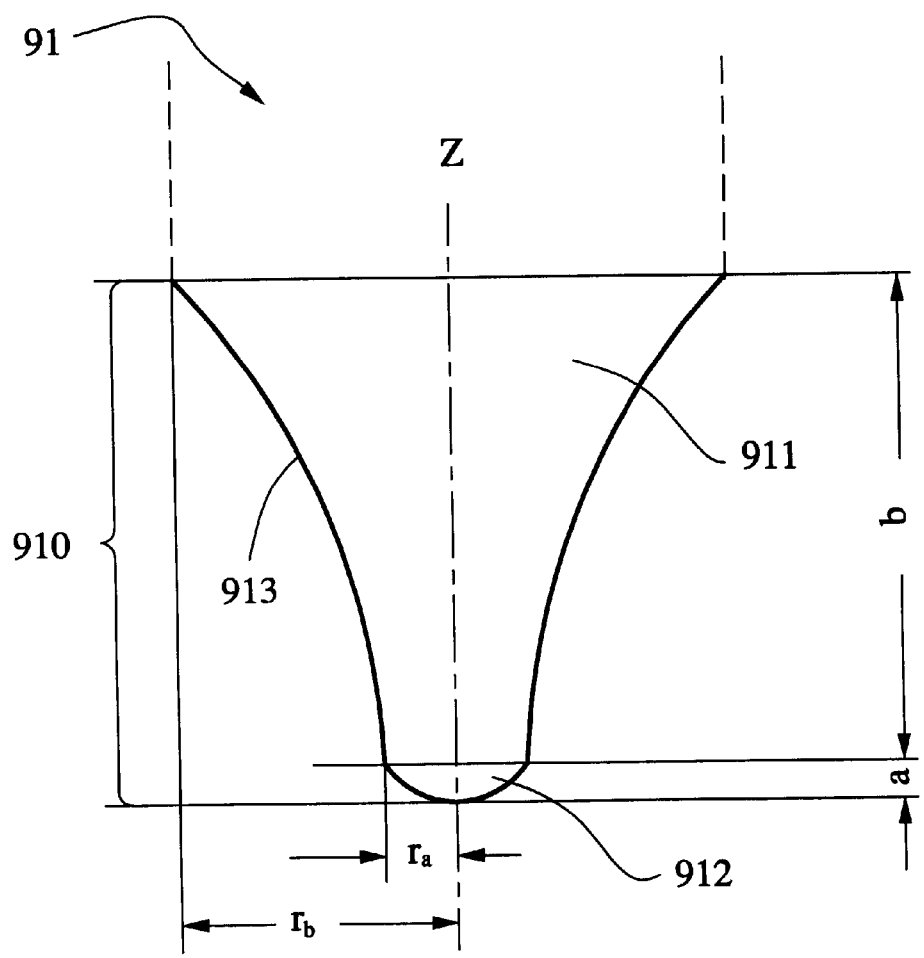
FIG. 9 illustrates an embodiment of the present invention.

FIG. 9 illustrates an embodiment according to the present invention. As illustrated, the surgical probe 91 has a tip 910 with a concave body portion 911 and a distal portion 912. The peripheral line or generatrix 913 can be circular, elliptic, parabolic, hyperbolic, their combinations or any other regular or irregular concave curves that fulfill the definition of a concave body portion in accordance with the present invention. In FIG. 9, Z is the longitudinal axis of the probe 91, a is the longitudinal length of the distal portion 12, b is the longitudinal length of the concave body portion 911, $r_a$ is the maximum radius of the distal portion 912 and $r_b$ is the maximum radius of the concave body portion 911 of the tip 910.

The length b of the concave body portion 911 can be similar in dimension to the length a of the distal portion 912 in longitudinal direction as long as a concave body portion 911 can be obtained and the physical essence of the present invention can be fulfilled. Also the maximum radius $r_b$ of the concave body portion 911 can be similar in dimension to the maximum radius $r_a$ of the distal portion 912 as long as a concave body portion 911 can be obtained and the physical essence of the present invention can be fulfilled.

In another embodiment of the present invention, the length b of the concave body portion 911 is preferably substantially larger than the length a of the distal portion 912 in longitudinal direction and the maximum radius $r_b$ of the concave body portion 911 is preferably substantially larger than the maximum radius $r_a$ of the distal portion 912.

The concave body portion 911 of the tip 910 is generally symmetrical with respect to the longitudinal axis Z of the probe 91. However, the concave body portion 911 can also be asymmetrical with respect to longitudinal axis Z of the probe 91.

Referring to FIG. 9, the distal portion 912 of the tip 910 can be substantially flat, concave, partially concave, convex, partially convex or any other regular or irregular distal shapes. The distal portion 912 can also have a shape selected from the group consisting essentially of plane, partial-sphere, hemisphere, pyramid, cone and cylinder. The distal portion 912 of the tip 910 is generally symmetrical with respect to the longitudinal axis Z of the probe 91. However, the distal portion 912 can also be asymmetrical with respect to longitudinal axis Z of the probe 91.

According to one example of the embodiment, an electric probe 91 has a tip 910 with a concave body portion 911 and a distal portion 912, wherein the longitudinal length b of the concave body portion 911 is about 0.3 mm, the longitudinal length a of the distal portion 912 is about 0.05 mm, the maximum radius $r_b$ of the concave body portion 911 is about 0.15 mm and the maximum radius $r_a$ of the distal portion 912 is about 0.05 mm. In this example, b and $r_b$ are substantially larger than a and $r_a$ respectively.

Figure 10:
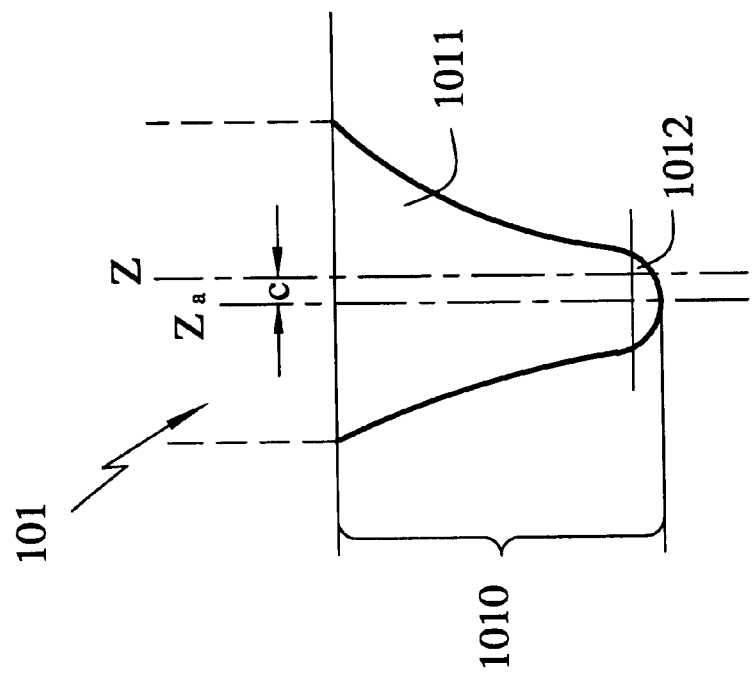
FIG. 10 illustrates another embodiment of the present invention with a concave body portion which is asymmetrical with respect to longitudinal axis of the probe.

FIG. 10 illustrates another embodiment of the present invention. As illustrated, both the concave body portion 1011 and the distal portion 1012 of the tip 1010 are asymmetrical with respect to the longitudinal axis Z of the probe 101. The longitudinal axis $Z_a$ of the distal portion 1012 is horizontally shifted with a distance of c with respect to the longitudinal axis Z of the probe 101.

Figure 11:
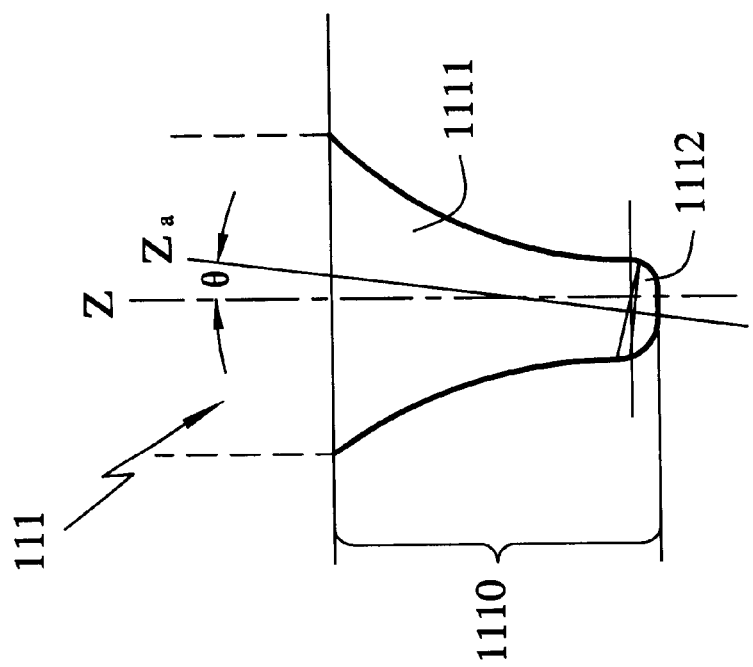
FIG. 11 illustrate another embodiment of the present invention with a concave body portion which is bent towards one side of the probe.

FIG. 11 illustrates another embodiment of the present invention. As illustrated, both the concave body portion 1111 and the distal portion 1112 of the tip 1110 are bent towards one side of the probe 111. There is a bending angle θ between he longitudinal axis $Z_a$ of the distal portion 1112 and the longitudinal axis Z of the probe 111. Generally, the bending angle θ is not larger than 30°. However, the bending angle θ can be larger than 30° if a concave body portion 1111 can still be obtained and the physical essence of the present invention can still be fulfilled.

According to the present invention, a concave body portion can also be constructed by two or more stages stacked together substantially along the longitudinal direction of the probe. Each stage itself is not necessarily a concave body portion.

Figure 12C:
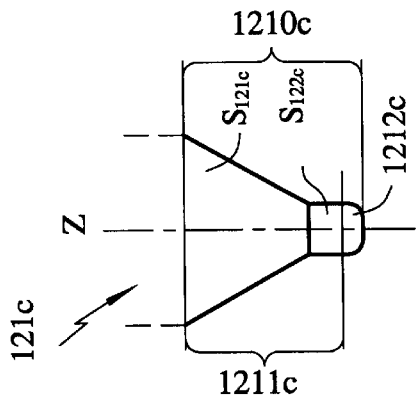
FIG. 12c illustrates another embodiment of the present invention with a concave body portion having a conical stage and a cylindrical stage.
Figure 12B:
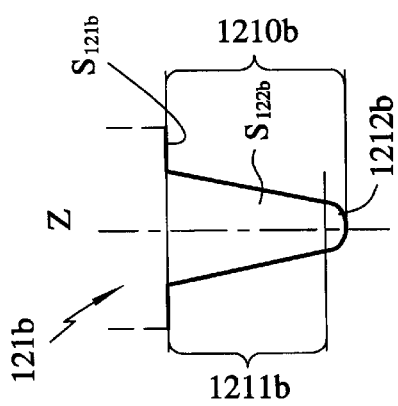
FIG. 12b illustrates another embodiment of the present invention with a concave body portion having a planar stage and a conical stage.
Figure 12E:
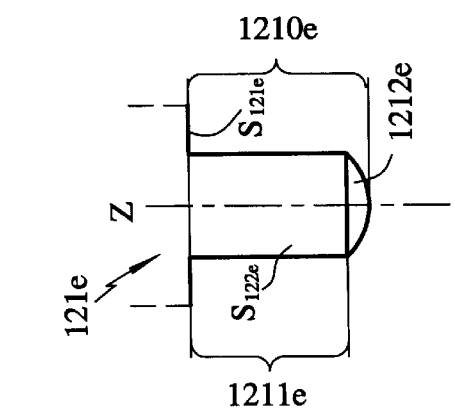
FIG. 12e illustrates another embodiment of the present invention with a concave body portion having a planar stage and a cylindrical stage.
Figure 12A:
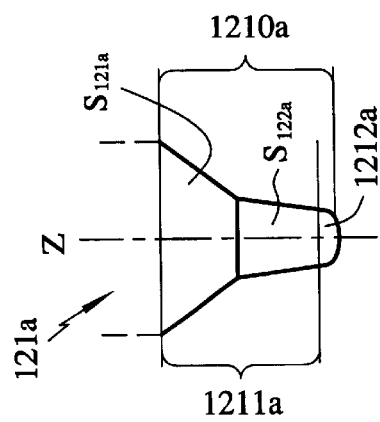
FIG. 12a illustrates another embodiment of the present invention with a concave body portion having two conical stages.
Figure 12D:
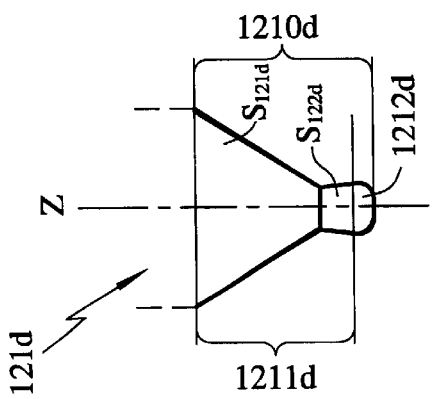
FIG. 12d illustrates another embodiment of the present invention with a concave body portion having two conical stages.

FIG. 12a illustrates another embodiment of the present invention. In FIG. 12a, the probe 121a has a tip 1210a having a distal portion 1212a and a concave body portion 1211a with two conical stages, $S_{121a}$ and $S_{122a}$. FIG. 12b illustrates another embodiment of the present invention. In FIG. 12b, the probe 121b has a tip 1210b having a distal portion 1212b and a concave body portion 1211b with one planar stage $S_{121b}$ and one conical stage $S_{122b}$. FIG. 12c illustrates another embodiment of the present invention. In FIG. 12c, the probe 121c has a tip 1210c having a distal portion 1212c and a concave body portion 1211c with one conical stage $S_{121c}$ and one cylindrical stage $S_{122c}$. FIG. 12d illustrates another embodiment of the present invention. In FIG. 12d, the probe 121d has a tip 1210d having a distal portion 1212d and a concave body portion 1211d with two conical stages, $S_{121d}$ and $S_{122d}$. FIG. 12e illustrates another embodiment of the present invention. In FIG. 12b, the probe 121e has a tip 1210e having a distal portion 1212e and a concave body portion 1211e with one planar stage $S_{121e}$ and one cylindrical stage $S_{122e}$.

In order to construct a concave body portion, the upper stage can be a conical stage with decreasing diameter towards the distal portion ($S_{121a}$ in FIG. 12a, $S_{121c}$ in FIG. 12c and $S_{121d}$ in FIG. 12d), a planar stage ($S_{121b}$ in FIG. 12b and $S_{121e}$ in FIG. 12e), a concave body portion itself, their combinations or any other possible regular or irregular shapes. The lower stage can be a conical stage with decreasing diameter towards the distal portion ($S_{122a}$ in FIG. 12a), a conical stage with increasing diameter towards the distal portion ($S_{122d}$ in FIG. 12d), a cylindrical stage ($S_{122c}$ in FIG. 12c and $S_{122e}$ in FIG. 12e), a concave body portion itself, their combinations or any order regular or irregular shapes. A concave body portion can be realized by any combination of possible shapes of upper stage and lower stage as long as they fulfill the definition of a concave body portion in the present invention.

Figure 13:
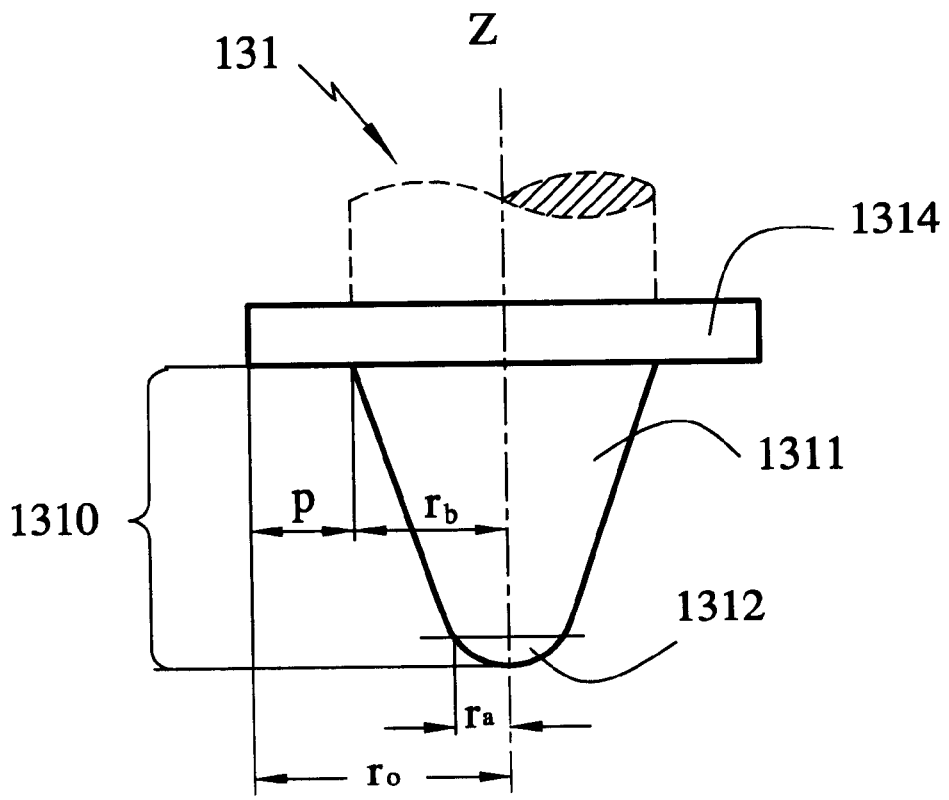
FIG. 13 illustrates yet another embodiment of the present invention having an obstacle.

FIG. 13 illustrates another embodiment of the present invention. As illustrated, the surgical probe 131 has a tip 1310 and an obstacle 1314, wherein the tip 1310 has a body portion 1311 and a distal portion 1312. The obstacle 1314 can be a ring positioned on back/upper part of the body portion 1311 or slightly after the body portion 1311. This obstacle 1314 is preferably positioned at a distance close to the radius of the bubble at maximum expansion phase (see also FIG. 6c).

Referring to FIG. 13, $r_o$ is the maximum radius of the obstacle 1314, $r_a$ is the maximum radius of the distal portion 1312 and $r_b$ is the maximum radius of the body portion 1311 of the tip 1310. As the obstacle 1314 is positioned on the out surface of the probe 131, maximum radius $r_o$ of the obstacle 1314 is larger than the maximum radius $r_b$ of the body portion 1311. P is the protruding length of the obstacle 1314 outside the probe 131.

The maximum radius $r_o$ of the obstacle 1314 can be similar in dimension to the maximum radius $r_a$ of the distal portion 1312 as long as an effect similar to that of a concave body portion can be realized by the cooperation of the obstacle 1314 and the body portion 1311 and the physical essence of the present invention can still be fulfilled. The protruding length P is preferably comparable in dimension to the maximum radius ($R_{maxbubble}$) of the cavitation bubble.

In another embodiment of the present invention, the maximum radius $r_o$ of the obstacle 1314 is preferably substantially larger than the maximum radius $r_a$ of the distal portion 1312.

When working with an obstacle 1314, the body portion 1311 of the tip 1310 can have a cylindrical portion, or a conical portion, or a concave portion, or a convex portion, or their combination, or any other possible regular or irregular shapes as long as they can cooperate with the obstacle 1314 to fulfill the physical essence of decelerating the liquid jet flow of the present invention. The body portion 1311 of the tip 1310 is generally symmetrical with respect to the longitudinal axis of the probe 131. However, the body portion 1311 can also be asymmetrical with respect to longitudinal axis Z of the probe 131.

Still referring to FIG. 13, the distal portion 1312 of the tip 1310 can be substantially flat, concave, partially concave, or convex or any other possible regular or irregular shapes. The distal portion 1312 can have a shape selected from the group consisting essentially of plane, partial-sphere, hemisphere, pyramid, cone and cylinder. The distal portion 1312 of the tip 1310 is generally symmetrical with respect to the longitudinal axis of the probe 131. However, the distal portion 1312 can also be asymmetrical with respect to longitudinal axis Z of the probe 131. Also, the body portion 1311 of the tip 1310 can comprises two or more stages.

According to one example of the embodiment of the present invention, an electric probe 131 has a conical body portion 1311, a distal portion 1312 and an obstacle 1314, wherein the obstacle 1314 is a ring positioned just after the body portion 1311. In this embodiment, the out radius $r_o$ of the ring 1314 is 0.3 mm, the maximum radius $r_a$ of the distal portion 1312 is 0.05 mm and the maximum radius $r_b$ of the body portion 1311 of the tip 1310 is 0.1 mm. The protruding length P is 0.2 mm which is the difference between $r_o$ and $r_b$. In this example, $r_o$ of the ring 1314 is substantially larger than the maximum radius $r_a$ of the distal portion 1312.

In accordance with yet another embodiment of the present invention, formation of the forward-propagating liquid jet can also be prevented by placing an obstacle, e.g. a pick, on one side of and/or in front of the tip as shown in FIGS. 8a–8f. Cavitation bubble is attracted to such an obstacle and collapses on it without forming the forward propagating liquid jet flow. FIG. 16 illustrates a geometrical configuration of a probe 161 with a pick of the embodiment, wherein the pick 1614 has a base portion 1615 disposed substantially after a tip 1610, a side portion 1616 which is connected to the base portion 1615 and a front portion 1617 extending from the side portion 1616, the side portion 1616 is disposed along one side of the tip 1610, and the front portion 1617 is bent towards the tip 1610 such that the front portion 1617 of the pick 1614 is in front of the tip 1610. In one example of the embodiment, the angle α between the side portion 1616 and the front portion 1617 is about 30°.

In accordance with the present invention, the surgical probe of the present invention can be an electric probe, an optical wave-guide probe, any form of their combinations or any other possible surgical probe for use in liquid media. Also, the surgical probe of the present invention should not be considered limited to single-fiber or single-electrode type probe only, but rather should be considered to cover both single-type and array-type surgical probes familiar to those skilled in the art.

In the above embodiments, the outer surfaces of the body portion and distal portion of the tip should not be considered limited to smooth surfaces, but rather should be considered to cover any surface textures familiar to those skilled in the art. For examples, the outer surface of the tip can comprises any minor regular or irregular ripples, grooves, dents, or bulges. Also, the material of the surgical probe in accordance with the present invention should be considered to cover all possible materials, including soft and flexible materials, familiar to those skilled in the art.

The present invention should not be considered limited to the particular examples described above, but rather should be understood to cover all aspects of the present invention as fairly set out in the attached claims. Various modifications, equivalents, as well as numerous geometrical configurations to which the present invention may be applicable will be readily apparent to those of skill in the art to which the present invention is directed upon review of the present specification.

What is claimed is:

1. A surgical probe for use in a liquid medium, said probe comprising:
   a tip for emitting energy while immersed in said liquid medium causing the formation of a cavitation bubble around said tip, said tip comprising:
   a. a distal portion with a maximum radius $r_a$ of about 0.05 mm
   b. a concave body portion immediately adjacent said distal portion with a maximum radius $r_b$ of about 0.1, to 0.15 mm and a longitudinal length b of about 0.3 to 0.4 mm; and
   wherein said concavity of said body portion is selected such that a liquid flow resulting from the collapse of said bubble is substantially reduced.

2. The surgical probe of claim 1, wherein said concavity is provided by at least two stages stacked together along a longitudinal direction of said probe.

3. The surgical probe of claim 2, wherein said at least two stages are conical.

4. The surgical probe of claim 2, wherein said at least two stages comprise a substantially planar stage and a conical stage.

5. The surgical probe of claim 2, wherein said at least two stages comprise a substantially planar stage and a cylindrical stage.

6. The surgical probe of claim 2, wherein said at least two stages comprise a cylindrical stage and a conical stage.

7. The surgical probe of claim 1, wherein said concave body portion is substantially symmetrical with respect to a longitudinal axis of said probe.

8. The surgical probe of claim 1, wherein said concave body portion is asymmetrical with respect to a longitudinal axis of said probe.

9. The surgical probe of claim 1, wherein said distal portion comprises a shape selected from a group consisting essentially of substantial flat, concave, partial concave, convex and partial convex.

10. The surgical probe of claim 1, wherein said distal portion is substantially symmetrical with respect to a longitudinal axis of said probe.

11. The surgical probe of claim 1, wherein said distal portion is asymmetrical with respect to a longitudinal axis of said probe.

12. The surgical probe of claim 1, wherein said concave body portion and said distal portion are bent towards one side of said probe.

13. The surgical probe of claim 1, wherein said probe is selected from a group consisting essentially of an electro-surgical electric probe, an optical wave-guide probe and a combination of optical wave-guide probe and electro-surgical electric probe.

14. A surgical probe for use in a liquid medium, said probe comprising:
   a. a tip for emitting energy while immersed in said liquid medium causing the formation of a cavitation bubble around said tip, said tip comprising;
      i. a distal portion with a maximum radius $r_a$ of about 0.05 mm;
      ii. a body portion with a maximum radius $r_b$ of about 0.1 to 0.15 mm and a longitudinal length b of about 0.3 to 0.4 mm, wherein said body portion is positioned immediately adjacent said distal portion;
   b. an obstacle concentrically protruding out of said probe for up to about 0.4 mm corresponding to a maximum radius of said cavitation bubble; and
   wherein said obstacle is configured in conjunction with said tip such that a liquid flow resulting from a collapse of said bubble is substantially reduced.

15. The surgical probe of claim 14, wherein said obstacle is positioned on said body portion of said tip.

16. The surgical probe of claim 14, wherein said obstacle is positioned adjacent said body portion of said tip.

17. The surgical probe of claim 14, wherein said body portion comprises at least two stages stacked together along a longitudinal direction of said probe.

18. The surgical probe of claim 14, wherein said body portion comprises at least a conical portion.

19. The surgical probe of claim 14, wherein said body portion comprises at least a concave portion.

20. The surgical probe of claim 14, wherein said body portion comprises at least a convex portion.

21. The surgical probe of claim 14, wherein said body portion is substantially symmetrical with respect to a longitudinal axis of said probe.

22. The surgical probe of claim 14, wherein said body portion is asymmetrical with respect to a longitudinal axis of said probe.

23. The surgical probe of claim 14, wherein said distal portion comprises a shape selected from a group consisting essentially of substantial flat, concave, partial concave, convex and partial convex.

24. The surgical probe of claim 14, wherein said distal portion is substantially symmetrical with respect to a longitudinal axis of said probe.

25. The surgical probe of claim 14, wherein said distal portion is asymmetrical with respect to a longitudinal axis of said probe.

26. The surgical probe of claim 14, wherein said body portion and said distal portion are bent towards one side of said probe.

27. The surgical probe of claim 14, wherein said probe is selected from a group consisting essentially of an electro-surgical electric probe, an optical wave-guide probe and a combination of optical wave-guide probe and electro-surgical electric probe.

28. A surgical probe for use in a liquid medium, said probe comprising:
   a. a tip for emitting energy while immersed in said liquid medium causing the formation of a cavitation bubble around said tip, said tip comprising;
      i. a distal portion with a maximum radius $r_a$;
      ii. a body portion with a maximum radius $r_b$, wherein said body portion is positioned immediately adjacent said distal portion;

a pick extending from a base portion disposed on said probe in the proximity of said tip, said pick comprising a side portion which is connected to said base portion and disposed along one side of said tip, and a front portion extending from said side portion and further bent towards said tip such that said front portion is in front of said tip and in a distance to said distal portion that is less than about 0.4 mm.

* * * * *

UNITED STATES PATENT AND TRADEMARK OFFICE
CERTIFICATE OF CORRECTION

PATENT NO. : 6,730,075 B2
DATED : May 4, 2004
INVENTOR(S) : Palanker et al.

It is certified that error appears in the above-identified patent and that said Letters Patent is hereby corrected as shown below:

Column 1,
Line 5, please insert the following paragraph before "FIELD OF THE INVENTION"

-- STATEMENT REGARDING FEDERALLY SPONSORED RESEARCH OR DEVELOPMENT
This invention was made with Government support under contract EY12888 awarded by the National Institutes of Health. The Government has certain rights in this invention. --

Signed and Sealed this

Twenty-seventh Day of July, 2004

JON W. DUDAS
*Acting Director of the United States Patent and Trademark Office*